sinus partial pressure of oxygen increasing amount of a compound of the formula

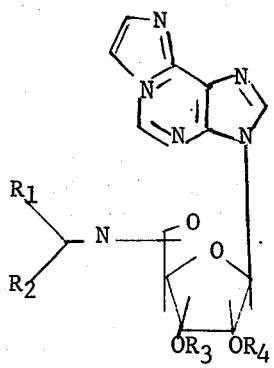

wherein $R_1$ and $R_2$ each are hydrogen, loweralkyl, a cycloalkyl of 3 to 6 carbon atoms, loweralkenyl or loweralkynyl and $R_3$ and $R_4$ each are hydrogen, acetyl, propionyl, butyryl, or $R_3$ and $R_4$ taken together form an isopropylidene or benzylidene moiety; or a pharmaceutically acceptable acid addition salt thereof, to said patient.

2. A method according to claim 1, wherein said compound is administered in a dosage of from 0.1 to 10.0 mg./kg. of body weight daily.

* * * * *

PREPARATIONS CONTAINING HEXOSES

This is a continuation application of application Ser. No. 93,592, filed Dec. 2, 1970, which in turn is a continuation application of Ser. No. 742,198, filed July 3, 1968, now abandoned.

BACKGROUND OF THE INVENTION

In surgical, anesthesiologic and internal medical practice, the infusion of solutions containing hexoses, especially glucose and fructose, of different concentrations, is widely used.

This administration has several purposes: in the first place, the large quantities of water which are thereby directly introduced into the veins compensate for the normal oral intake of liquids, which is often impaired or contra-indicated in patients who have recently undergone a surgery and in other severe cases; it also permits an equilibration of the water metabolism in order to obtain a satisfactory elimination of toxic catabolites which are abnormally accumulated or produced.

Drip infusions are, therefore, administered whenever a dehydrated patient needs an immediate supply of water or when an activation of the toxic catabolite elimination is required by increased diuresis; for example, drip infusions are used in cases of severe infectious diseases, especially when associated with hypotension, in toxic states, in states of shock, during surgery and in post-operative periods. Especially good results are obtained in pediatric toxic states, in cases of acute diarrhoea and in cases of infectious diseases.

A further object of the drip infusion of hexoses is that of compensating the volumetric deficit following both traumatic and surgically spontaneous hemorrhages, which is a deficit which should be immediately compensated in order to avoid irreparable damage to the patient.

The third object which is strictly related to the chemical nature of the drip infusions themselves, is that of supplying easily utilisable metabolites, usually hexoses, of high calorific value.

Since, as is known, glucides provide an immediate source of energy, glucose solutions administered by infusion constitute a ready source of calories, which is a very important fact because patients treated by infusions often cannot be fed. Furthermore, hexoses, and especially glucose, represent the key substances of three metabolic systems, namely, glucidic, proteic and lipid metabolism; they are used in the synthesis of glycogen, the anti-toxic action of which at the level of the liver cell is very well known and the decrease of which occurs during anesthesia; starting from glucose, d-ribose is anabolised, this being a pentose which participates in the structure of nucleotides and nucleic acids and another glucide, i.e. galactose, is present in the molecules of cerebrosides molecules. In other words, glucides fulfil essential structural and metabolic functions in cells and organs, as well as in the functions thereof.

Infusions of carbohydrates are administered in order to supply the organism with energy and to correct the intermediate metabolic processes which have been altered, for example, by the use of anesthetics, which is shown by an increase of ketonic bodies in the blood.

However, the administration of the ordinary glucose infusions is not always free from side effects; one of these is the increase of the blood sugar level followed by glycosuria, which is an indication of a defective metabolic utilisation of the glucides injected. Although this glycosuria is not great, it cannot be clinically underestimated since it may cause, among other things, an abnormal increase in diuresis, which may, in turn, lead to cellular dehydration and sodium depletion. Although the stimulation of diuresis is advisable in cases of water retention, it is, however, harmful to patients showing hypotension, water inbalance, hemorrhage and the like, since rehydration of the patient, which is one of the objects of the administration, would be impaired.

It is an object of the present invention to provide new compositions which overcome the above-mentioned disadvantages which arise in the oral and parenteral administration of glucides.

SUMMARY OF THE INVENTION

The present invention provides new compositions comprising at least one glucide, together with at least one phosphorylated glucide in the form of a non-toxic, physiologically compatible salt.

DETAILED DESCRIPTION OF THE INVENTION

As examples of glucides which can be used in the new compositions according to the present invention, there may be mentioned glucose, fructose, lactose and galactose. Examples of phosphorylated glucides which can be used include glucose-1-phosphate, glucose-6-phosphate, fructose-1,6-diphosphate, 6-phosphogluconate and ribose-5-phosphate.

As examples of salts of phosphorylated glucides which can be used, there may be mentioned the alkali metal salts, such as the sodium and potassium salts, and the alkaline earth metal salts, such as the calcium salts, as well as the salts with organic nitrogen bases, such as the mono-, di- and trialkylamines, the mono-, di- and trihydroxyalkylamines and heterocyclic organic bases, such as morpholine, pyrrolidine and N-hydroxy-ethyl-piperazine.

As is known, the phosphorylated glucides, especially glucose-1-phosphate, have a special biochemical and clinical character since they may even be metabolised by patients suffering from diabetes mellitus without any insulin activity due to their phosphorylation. However, in the case of normal sugars, they must be previously phosphorylated by the action of insulin and other catalysts in order to be metabolised.

In diabetes, there is a block in the phosphorylation process to the detriment of glucose, which cannot be metabolised without previous phosphorylation to glucose-1-phosphate. Consequently, an accumulation of glucose in blood (hyperglycemia) is observed, followed by glycosuria.

The salts of glucose-1-phosphate or of at least one other phosphorylated glucide, when associated with ordinary glucide solutions, act as metabolic catalysts, with the result that the glucide administered is completely utilised and a reduced glycosuria occurs, if at all: the considerable clinical advantages are obvious.

An important aspect of the new compositions according to the present invention is that, after administration thereof, the Staub-Traugott effect does not occur, i.e. there is no hypoglycemia following the period of hyperglycemia, which is very frequent in subjects treated with simple hexoses. The absence of the Staub-Tragott effect following the administration of the compositions comprising glucides and phosphorylated glucides according to the present invention, indicates un- 8. A sterile aqueous solution of the composition of claim 4, containing a therapeutically effective amount thereof up to about 6% by weight.

9. A composition according to claim 1 wherein the alkali metal salt is the sodium or potassium salt.

10. A composition according to claim 2 wherein the alkali metal salt is the sodium of potassium salt.

11. A composition according to claim 3 wherein the alkali metal salt is the sodium or potassium salt.

12. A composition according to claim 4 wherein the alkali metal salt is the sodium or potassium salt.

* * * * *